(12) United States Patent
Godo et al.

(10) Patent No.: US 9,186,054 B2
(45) Date of Patent: Nov. 17, 2015

(54) ENDOSCOPE APPARATUS INCLUDING A PLURALITY OF LIGHT-EMITTING DEVICES

(71) Applicant: OLYMPUS CORPORATION, Tokyo (JP)

(72) Inventors: Hirokazu Godo, Hachioji (JP); Yoshinori Ikeda, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 9 days.

(21) Appl. No.: 13/952,814

(22) Filed: Jul. 29, 2013

(65) Prior Publication Data

US 2014/0031624 A1 Jan. 30, 2014

Related U.S. Application Data

(63) Continuation of application No. PCT/JP2012/073829, filed on Sep. 18, 2012.

(30) Foreign Application Priority Data

Feb. 17, 2012 (JP) .................. 2012-032902

(51) Int. Cl.
*A61B 1/045* (2006.01)
*A61B 1/06* (2006.01)
(Continued)

(52) U.S. Cl.
CPC ........... *A61B 1/0638* (2013.01); *A61B 1/00186* (2013.01); *A61B 1/0646* (2013.01); *A61B 1/0669* (2013.01); *A61B 1/0684* (2013.01);
(Continued)

(58) Field of Classification Search
CPC ...... A61B 1/043; A61B 1/045; A61B 1/0638; A61B 1/0646; A61B 1/0684

USPC ................... 600/178, 180, 181, 118
See application file for complete search history.

(56) References Cited

U.S. PATENT DOCUMENTS 5,187,572 A * 2/1993 Nakamura et al. .............. 348/68
7,235,045 B2 * 6/2007 Wang et al. .................... 600/109
(Continued)

FOREIGN PATENT DOCUMENTS

EP 1 908 393 A1 4/2008
EP 2 283 769 A1 2/2011
(Continued)

OTHER PUBLICATIONS

Extended Supplementary European Search Report dated Sep. 8, 2015 from related European Application No. 12 86 8915.5.

*Primary Examiner* — John P Leubecker
(74) *Attorney, Agent, or Firm* — Scully, Scott, Murphy & Presser, P.C.

(57) ABSTRACT

An endoscope apparatus according to a present embodiment has a CCD and an LED control section which controls LED1 and LED2. The LED control section sequentially drives the two LEDs, LED1 and LED2, on the basis of an image pickup start timing signal corresponding to each image pickup cycle S for the CCD within the image pickup cycle S such that driving time periods for LED1 and LED2 do not overlap. The LED control section also variably controls the driving time periods for LED1 and LED2 to adjust an amount of exposure within the image pickup cycle S and performs control so as to conduct, within the image pickup cycle S, at least a first drive within the image pickup cycle S of LED2 that is a second or subsequent one to be driven with reference to a timing for driving of LED1 that is driven earlier.

11 Claims, 7 Drawing Sheets

(51) Int. Cl.
*G02B 23/24* (2006.01)
*G02B 26/00* (2006.01)
*A61B 1/00* (2006.01)
*A61B 1/04* (2006.01)

(52) U.S. Cl.
CPC ........ *G02B 23/2469* (2013.01); *G02B 23/2484* (2013.01); *G02B 26/007* (2013.01); *A61B 1/043* (2013.01); *A61B 1/045* (2013.01)

(56) References Cited

U.S. PATENT DOCUMENTS

| | | | |
|---|---|---|---|
| 7,365,781 B2 * | 4/2008 | Kubota et al. | 348/231.9 |
| 7,746,405 B2 * | 6/2010 | Yuyama et al. | 348/370 |
| 7,846,091 B2 * | 12/2010 | Fulghum | 600/160 |
| 8,734,335 B2 * | 5/2014 | Kobayashi | 600/178 |
| 2002/0062064 A1 * | 5/2002 | Nakamura et al. | 600/178 |
| 2004/0027459 A1 | 2/2004 | Segawa et al. | |
| 2005/0197532 A1 * | 9/2005 | Sasaki et al. | 600/160 |
| 2006/0089554 A1 * | 4/2006 | Ishihara et al. | 600/476 |
| 2007/0219435 A1 * | 9/2007 | Segawa et al. | 600/302 |
| 2008/0306343 A1 * | 12/2008 | Yamazaki | 600/180 |
| 2010/0002292 A1 * | 1/2010 | Yabe et al. | 359/388 |
| 2010/0201797 A1 | 8/2010 | Shizukuishi et al. | |
| 2010/0217077 A1 | 8/2010 | Gono | |
| 2011/0034770 A1 | 2/2011 | Endo et al. | |
| 2011/0069199 A1 * | 3/2011 | Yamazaki | 348/229.1 |
| 2011/0071352 A1 * | 3/2011 | Ozawa et al. | 600/109 |
| 2011/0158914 A1 * | 6/2011 | Yamada | 424/9.6 |
| 2013/0113911 A1 * | 5/2013 | Hanano et al. | 348/79 |

FOREIGN PATENT DOCUMENTS

| | | |
|---|---|---|
| JP | 63-096623 A | 4/1988 |
| JP | 63-288130 A | 11/1988 |
| JP | 11-299731 A | 11/1999 |
| JP | 2005-185513 A | 7/2005 |
| JP | 2007-029555 A | 2/2007 |
| JP | 2007-029746 A | 2/2007 |
| JP | 2009-66121 A | 4/2009 |
| JP | 2010-29383 A | 2/2010 |
| JP | 2010-194291 A | 9/2010 |
| JP | 2010-227200 A | 10/2010 |
| JP | 2011-036361 A | 2/2011 |
| WO | WO 2007/013245 A1 | 2/2007 |

* cited by examiner

ENDOSCOPE APPARATUS INCLUDING A PLURALITY OF LIGHT-EMITTING DEVICES

CROSS REFERENCE TO RELATED APPLICATION

This application is a continuation application of PCT/JP2012/073829 filed on Sep. 18, 2012 and claims benefit of Japanese Application No. 2012-032902 filed in Japan on Feb. 17, 2012, the entire contents of which are incorporated herein by this reference.

BACKGROUND OF THE INVENTION

1. Field of the Invention

The present invention relates to an endoscope apparatus having a plurality of illumination sections that emit illuminating light, with which a site to be observed is irradiated, and a control section which controls driving of the plurality of illumination sections.

2. Description of the Related Art

Among endoscope apparatuses, a so-called electronic endoscope apparatus is generally known which has an illumination section emitting illuminating light and obtains an image signal corresponding to an image of an object by irradiating a site to be observed with light emitted from the illumination section as illuminating light, receiving return light of the illuminating light reflected from the object with a solid image pickup device, such as a CCD (charge coupled device), (exposing the solid image pickup device to the return light), and photoelectrically converting the return light.

Among such electronic endoscope apparatuses, a so-called frame-sequential endoscope apparatus is generally known. The frame-sequential endoscope apparatus does not have a light-receiving side color filter at a front face of each light-receiving device of a solid image pickup device and irradiates a site to be observed with illuminating lights of a plurality of colors required for formation of an endoscopic image in sequence. The frame-sequential endoscope apparatus exposes the solid image pickup device to light for one image pickup cycle with each irradiation operation with illuminating light, photoelectrically converts return light reflected from an object with the solid image pickup device, and obtains an image signal of a predetermined color for every image pickup cycle. The frame-sequential endoscope apparatus can obtain one endoscopic image by combining image signals of individual colors obtained in respective image pickup cycles.

Examples of the frame-sequential endoscope apparatus include a frame-sequential endoscope apparatus that has a light source apparatus in which a color wheel, having irradiation side color filters of respective colors for generating illuminating lights of a plurality of colors required for formation of an endoscopic image, is arranged, e.g., in front of a light source emitting white light and irradiates an object in rotation with illuminating lights of the plurality of colors, such as R, G, and B, from a distal end portion of an endoscope insertion portion via a light guide or the like by rotationally driving the color wheel.

In the endoscope apparatus with the above-described configuration, an irradiation time period and an irradiation cycle (timing for irradiation) for illuminating lights of the individual colors, such as R, G, and B, depend on a rotation cycle of the color wheel. The endoscope apparatus can obtain an endoscopic image with appropriate brightness by adjusting an exposure time period for the solid image pickup device within the irradiation time period in each of the determined irradiation cycles to obtain image signals of the individual colors.

For example, an endoscope apparatus proposed in Japanese Patent Application Laid-Open Publication No. 2007-29746 is conventionally available in order to reduce color misregistration or image blurring occurring in an endoscopic image.

The endoscope apparatus described in Japanese Patent Application Laid-Open Publication No. 2007-29746 allows selection of standard time periods, short time periods, or long time periods as a lighting time period for each of three LEDs emitting illuminating lights of respective colors of R, G, and B and an exposure time period for a solid image pickup device for obtaining an image signal for each color according to an observation situation in which return light from an object is bright or dark. The endoscope apparatus also performs control so as to change an image pickup cycle for the solid image pickup device and a lighting cycle (timing for lighting) for the LEDs for the individual colors of R, G, and B to standard cycles, short cycles, or long cycles according to selection of the time periods such that an observed image with an optimum image pickup cycle is obtained according to an observation situation. With the configuration, the endoscope apparatus reduces color misregistration and image blurring in an endoscopic image.

SUMMARY OF THE INVENTION

An endoscope apparatus according to one aspect of the present invention is an endoscope apparatus including a timing generator which outputs an index signal in predetermined cycles, an image pickup section which is driven on the basis of the index signal so as to pick up an image of a site to be observed for each of the predetermined cycles, a plurality of illumination sections which each have one or a plurality of light-emitting devices and emit illuminating light, with which the site to be observed is irradiated, and an illumination control section which controls driving of the plurality of illumination sections, wherein the light with which the site to be observed is irradiated by the individual illumination sections comprises lights of different colors, and the illumination control section performs control so as to sequentially drive the plurality of illumination sections such that driving time periods for the plurality of illumination sections do not overlap with each other or one another within one image pickup cycle which is a period from when the index signal is inputted to when a next index signal is inputted and performs control so as to conduct, within the image pickup cycle, at least a first drive within the image pickup cycle of one of the illumination sections which is a second or subsequent one to be driven with reference to a timing for driving of an illumination section which is driven earlier than the illumination section that is the second or subsequent one to be driven.

DETAILED DESCRIPTION OF THE PREFERRED EMBODIMENTS

Embodiments of the present invention will be described in detail below with reference to the drawings.

First Embodiment

Figure 1:
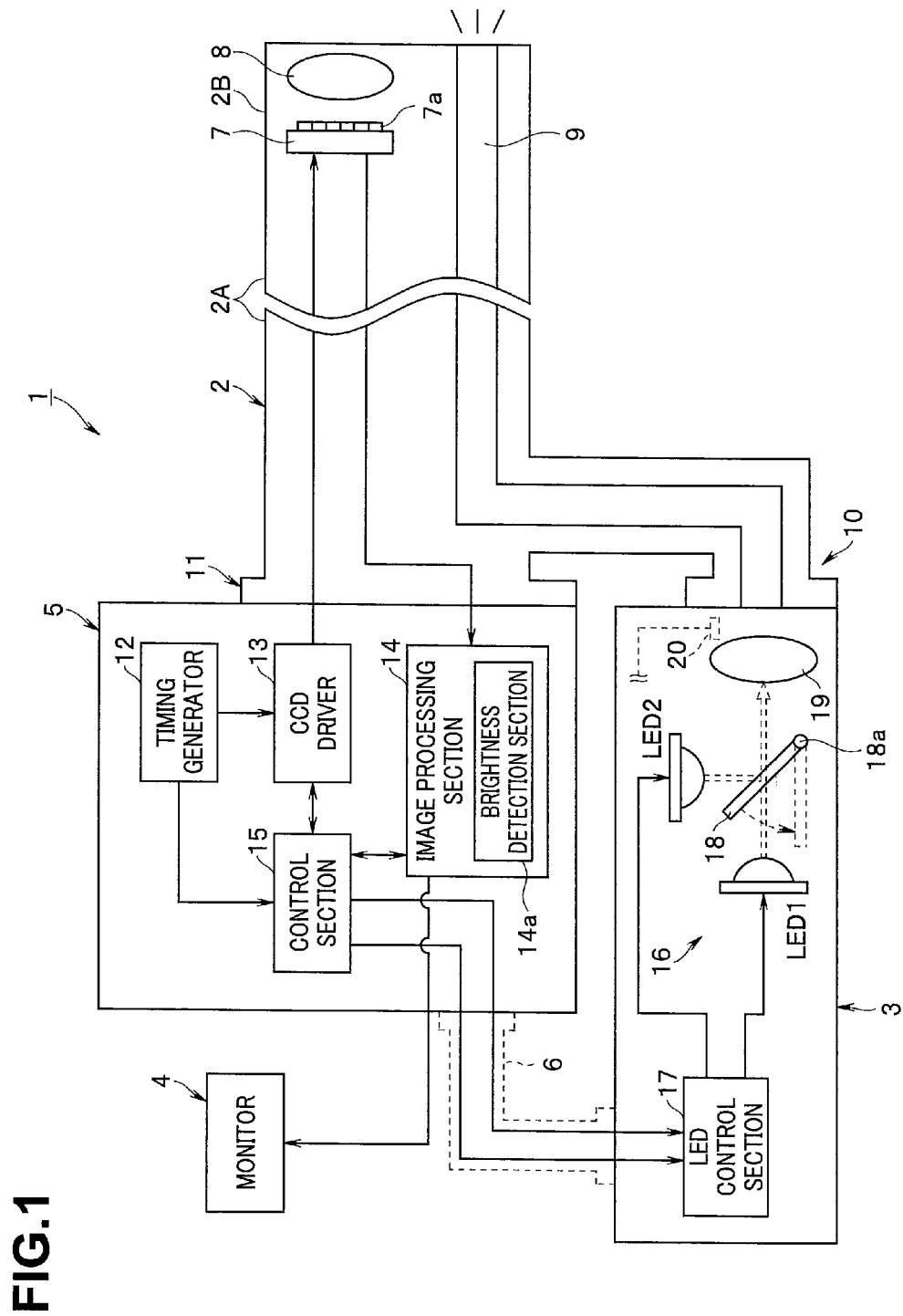
FIG. 1 is a block diagram showing a configuration of an endoscope apparatus according to a first embodiment of the present invention.

FIG. 1 is a block diagram showing a configuration of an endoscope apparatus according to a first embodiment of the present invention.

An endoscope apparatus 1 shown in FIG. 1 is configured to include an electronic endoscope (hereinafter referred to as an endoscope) 2 which is inserted into a body cavity to observe a site to be observed, a light source apparatus 3 which supplies normal light and special light to the endoscope 2, and a processor 5 which performs signal processing on an image signal obtained through image pickup by the endoscope 2 and causes the processed signal to be displayed on a monitor 4.

The endoscope 2 has a solid image pickup device such as a CCD (hereinafter referred to as a CCD) 7 which is a solid image pickup device provided at a distal end portion 2B of an insertion portion 2A to be inserted into a body cavity, an objective lens system 8 which is disposed in front of the CCD 7 of the distal end portion 2B, a light guide 9 which guides observation illuminating light to the distal end portion 2B of the insertion portion 2A, an operation switch (not shown) which is provided at an operation portion for operation of the endoscope 2, a connector portion 10 for connection to the light source apparatus 3, and an electric connector portion 11 for connection to the processor 5.

The endoscope apparatus 1 is capable of normal light observation with normal light and special-light observation with special light (narrow band observation (narrow band imaging: NBI) with narrow band light here).

The endoscope 2 has light-receiving side color filters 7a of a plurality of colors required for formation of an endoscopic image which are arranged with regularity at front faces of a plurality of light-receiving devices of the CCD 7.

The light-receiving side color filters 7a are complementary color filters. Image signals of the individual colors are obtained by using difference values among the amounts of return lights having transmitted the light-receiving side color filters 7a of the individual colors.

Note that the light-receiving side color filters 7a are not limited to complementary color filters. For example, light-receiving side color filters for normal light of, e.g., R, G, and B and at least one light-receiving side color filter for special light required for formation of an endoscopic image under special light may be disposed with predetermined regularity to obtain image signals of the individual colors. Alternatively, a light-receiving side color filter for normal light may also serve as a light-receiving side color filter for special light.

The light source apparatus 3 and the processor 5 each have a plurality of observation modes and support both a normal light observation mode and a special-light observation mode in particular. The endoscope apparatus 1 can perform normal light observation and special-light observation by using the light source apparatus 3 and the processor 5 in combination with the endoscope 2.

The processor 5 has a timing generator 12 for timing control for the entire endoscope apparatus 1, a CCD driver 13 which drives the CCD 7 in the endoscope 2, an image processing section 14 which processes an image signal from the CCD 7, a control section 15 which controls the whole of the endoscope apparatus 1, and input and display means (not shown), such as a keyboard and a front panel.

The timing generator 12 generates an index signal which is a timing signal for image pickup by the CCD 7 and supplies the index signal to the control section 15. The control section 15 controls the CCD driver 13 on the basis of the index signal to drive the CCD 7.

Note that the index signal is an image pickup start timing signal corresponding to each image pickup cycle S (see FIG. 2) for the CCD 7, i.e., a reference signal synchronous with an exposure period for the CCD 7 and is, for example, a vertical synchronizing signal, which is produced in cycles of once an endoscopic image for one field and one frame. The index signal is, of course, not limited to the vertical synchronizing signal described above, and a similar reference signal generated by different means may be used.

The image processing section 14 processes an image signal from the CCD 7 and outputs the processed signal to the monitor 4. With the operation, an endoscopic image is displayed on the monitor 4.

The image processing section 14 is provided with a brightness detection section 14a. The brightness detection section 14a determines brightness of an endoscopic image on the basis of image signals in a former image pickup cycle and outputs a detection result to the control section 15.

The control section 15 controls the CCD driver 13 on the basis of an index signal to drive the CCD 7. The control section 15 also controls signal processing by the image processing section 14 and causes an obtained endoscopic image to be displayed on the monitor 4.

The control section 15 performs communication with an LED control section 17 (to be described later) in the light source apparatus 3 via a signal cable 6 and exchanges various data with the LED control section 17.

In the present embodiment, the control section 15 outputs a brightness detection result from the brightness detection section 14a and an index signal from the timing generator 12 to the LED control section 17 in the light source apparatus 3.

Note that a brightness detection result may be directly outputted from the image processing section 14 to the LED control section 17 without the control section 15.

Although the timing generator 12, the CCD driver 13, the image processing section 14, and the control section 15 are separately configured in the present embodiment, some or all of the components may be configured as one component by using, for example, an FPGA (field programmable gate array).

The light source apparatus 3 is configured to include a light source unit 16 and the LED control section 17 that controls the light source unit 16.

The light source unit 16 has LED1 and LED2 constituting a plurality of illumination sections, each having one or a plurality of light-emitting devices, an optical filter 18, and a lens 19 for irradiating an end face of the light guide 9 with illuminating light from the optical filter 18.

Note that although an LED is used as a light-emitting device in the present embodiment, the present invention is not limited to an LED, and a laser diode or an organic EL may be used instead.

LED1 is, for example, an LED which emits white light, and LED2 is, for example, an LED which emits violet (V) light. That is, in the endoscope apparatus 1 according to the present embodiment, the two LEDs, LED1 and LED2, are provided as the plurality of illumination sections in order to perform special-light observation, such as narrow band observation.

Note that the plurality of illumination sections are not limited to the two LEDs, LED1 and LED2. For example, the plurality of illumination sections may be configured by providing three or more LEDs such that a necessary luminescent color is obtained.

The optical filter 18 has an optical property of converting white light from LED1 into green (G) and irradiating the lens 19 with the light and reflecting violet light from LED2 and irradiating the lens 19 with the light.

That is, in the endoscope apparatus 1 according to the present embodiment, the two LEDs, LED1 and LED2, as the plurality of illumination sections and the optical filter 18 are provided in order to obtain green (G) light and violet light required to perform special-light observation, such as narrow band observation.

The optical filter 18 is configured to be pivotable about a shaft 18a as a fulcrum so as to retreat from inside an optical path of light from LED1.

That is, in the endoscope apparatus 1 in FIG. 1, a position where the optical filter 18 is arranged indicates a state in which special-light observation, such as narrow band observation, is to be performed.

If normal light observation is performed with normal light that is white light, when switching to the normal light observation mode is performed through an operation at the operation portion (not shown) of the endoscope 2, the control section 15 in the processor 5 outputs a control signal for executing the normal light observation mode to the LED control section 17 in the light source apparatus 3. Upon receipt of the control signal, the LED control section 17 controls a drive section (not shown) which applies driving force to the optical filter 18. With the control, the optical filter 18 retreats from inside the optical path for LED1 and is arranged at a retreat position (a position indicated by a broken line in FIG. 1). The lens 19 is irradiated with white light only from LED1, and white light required for normal light observation is obtained.

The lens 19 irradiates the end face of the light guide 9 with incident light. With the irradiation, illuminating light from the light source unit 16 is transmitted to the distal end portion 2B of the endoscope 2 by the light guide 9, and an object is irradiated with the illuminating light.

The LED control section 17 serving as an illumination control section performs lighting control on LED1 and LED2 in the light source unit 16 on the basis of a brightness detection result from the brightness detection section 14a in the processor 5 and an index signal from the timing generator 12. The LED control section 17 also controls the drive section (not shown) on the basis of a control signal from the control section 15 such that the optical filter 18 is arranged at a position corresponding to normal light observation or special-light observation.

Note that although control of the light source unit 16 in the endoscope apparatus 1 has been described as being performed by the LED control section 17 in the present embodiment, the control section 15 in the processor 5 and the LED control section 17 in the light source apparatus 3 may each be composed of, e.g., an FPGA (field programmable gate array).

When normal light observation is performed in the endoscope apparatus 1 according to the present embodiment, the LED control section 17 does not light LED2 and drives LED1 on the basis of an index signal which is an image pickup start timing signal corresponding to each image pickup cycle for the CCD 7. The LED control section 17 also variably controls a driving time period for LED1 to adjust an amount of exposure within the image pickup cycle described above.

That is, the LED control section 17 stores, for example, standard brightness in one image pickup cycle. The LED control section 17 calculates a lighting period for LED1 on the basis of a difference between the brightness and a brightness detection result which indicates brightness of a previous field or a previous frame and drives LED1.

With the driving, an object is irradiated with white light as normal light, and the CCD 7 is exposed to return light of the irradiating light for one image pickup cycle. The CCD 7 performs photoelectric conversion on the basis of components of the return light which have passed through the light-receiving side color filters 7a and obtains image signals of the individual colors in the one image pickup cycle. The image signals of the individual colors are combined, and an endoscopic image under normal light observation in one image pickup cycle is obtained.

When special-light observation is performed in the endoscope apparatus 1 according to the present embodiment, the LED control section 17 successively and sequentially drives the two LEDs, LED1 and LED2, on the basis of an index signal which is an image pickup start timing signal corresponding to each image pickup cycle for the CCD 7 such that driving time periods for LED1 and LED2 do not overlap with each other. The LED control section 17 variably controls the driving time periods for the two LEDs, LED1 and LED2, in order to adjust an amount of exposure within the image pickup cycle. The LED control section 17 performs control so as to conduct, within the image pickup cycle, at least a first drive within the image pickup cycle of LED2 that is a second or subsequent one to be driven with reference to a timing for driving of LED1 that is driven earlier.

In the case, the LED control section 17 performs control so as to conduct, within the image pickup cycle, at least the first drive within the image pickup cycle of LED2 that is the second or subsequent one to be driven substantially at a same time as a timing for stopping of driving of LED1 that is driven earlier.

That is, the endoscope apparatus 1 has a plurality of observation modes, and whether to light each of the plurality of LEDs is controlled according to an observation mode designated or selected by a user.

An example of such lighting control of LED1 and LED2 by the LED control section 17 will be described with reference to FIGS. 1 and 2.

Figure 2:
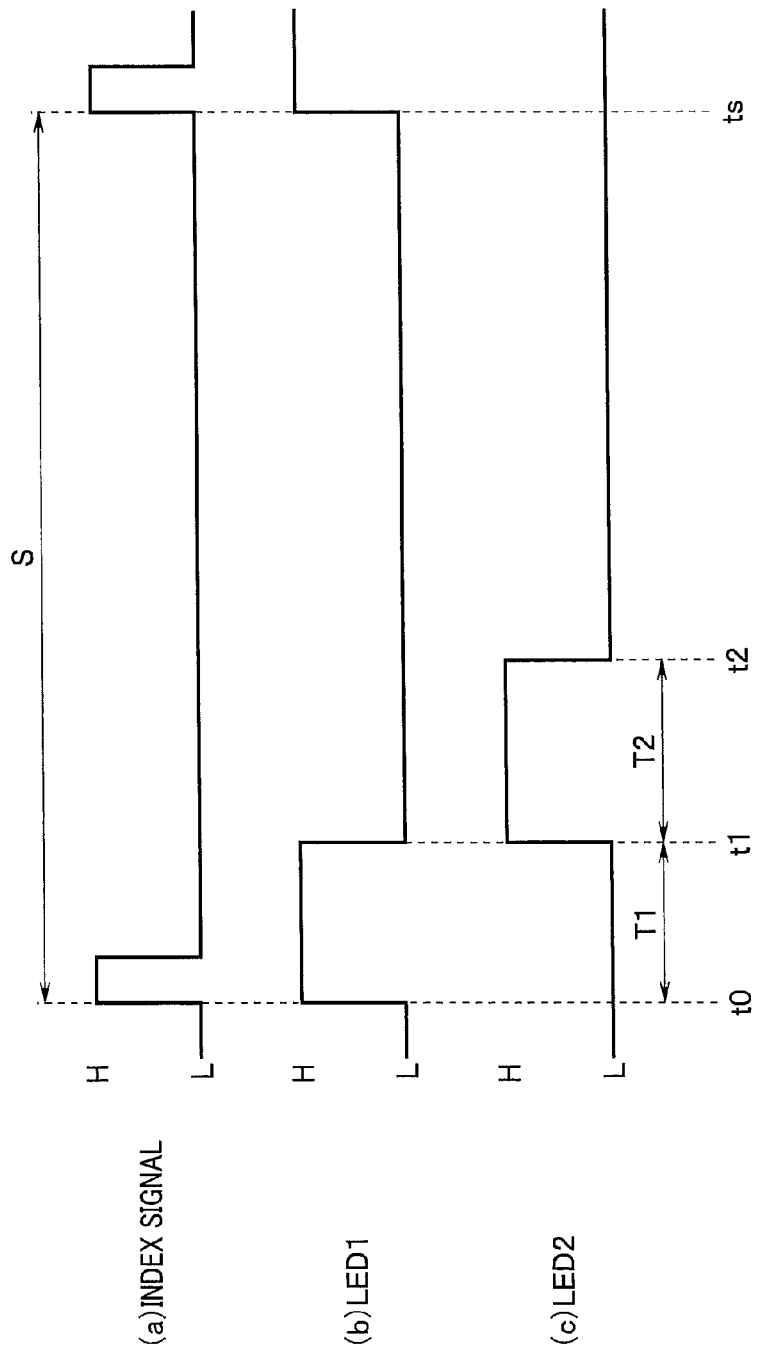
FIG. 2 is intended to explain action of the endoscope apparatus in FIG. 1 and is a timing chart for an index signal, LED1, and LED2.

FIG. 2 are timing charts for explaining action of the endoscope apparatus in FIG. 1. FIG. 2(a) shows an index signal, FIG. 2(b) shows a driving signal for LED1, and FIG. 2(c) shows a driving signal for LED2. Note that "High" level in FIG. 2 indicates an on status of a signal while "Low" level indicates an off status of the signal.

Assume a case where after the endoscope apparatus 1 shown in FIG. 1 is powered on, the insertion portion 2A is inserted into a body cavity, and special-light observation with narrow band light is performed on a site to be observed inside the body cavity.

In the case, the endoscope apparatus 1 according to the present embodiment performs lighting control of the light source unit 16 in the light source apparatus 3 with timing as shown in FIG. 2.

That is, when an index signal with timing as shown in FIG. 2(*a*) from the timing generator 12 in the processor 5 and a brightness detection result from the brightness detection section 14*a* are supplied to the LED control section 17 in the light source apparatus 3, the LED control section 17 first calculates respective lighting periods T1 and T2 for LED1 and LED2 on the basis of the brightness detection result within an image pickup cycle S (a shown period from time t0 to time ts) for the CCD 7 which depends on an index signal that is an image pickup start timing signal.

In the case, the LED control section 17 stores, for example, standard brightness in one image pickup cycle and calculates the lighting period T1 for LED1 and the lighting period T2 for LED2 on the basis of a difference between the brightness and a brightness detection result which indicates brightness of a previous field or a previous frame. That is, the LED control section 17 calculates driving time periods for the individual illumination sections on the basis of a difference between the predetermined brightness in one image pickup cycle and brightness of a field or a frame in an image pickup cycle previous to an image pickup cycle in question.

After the lighting periods T1 and T2 for the individual LEDs, LED1 and LED2, are determined, the LED control section 17 causes LED1 to emit light at time t0 when an index signal shown in FIG. 2(*a*) changes to "High" level (see FIG. 2(*b*)). White light emitted by LED1 is converted into green (G) light by the optical filter 18, and the green light is made by the lens 19 to come incident on the end face of the light guide 9.

After a lapse of the lighting period T1 for LED1, i.e., at time t1, the LED control section 17 performs control so as to extinguish LED1 and at a same time light LED2 (see FIGS. 2(*a*) and 2(*b*)). A timing for lighting of LED2 may be controlled with reference to the lighting time period for LED1 or extinction of LED1.

That is, LED2 is lighted at a same time as extinction of LED1 even within a lighting permission period (time t0 to time ts) for LED1.

At time t1, violet light emitted from LED2 is reflected by the optical filter 18 and is made by the lens 19 to come incident on the end face of the light guide 9. LED2 is kept on during the calculated lighting period T2, i.e., until time t2.

With the series of operations, an object is sequentially irradiated with green (G) light and violet light that are each special light within one image pickup cycle for the CCD 7. The CCD 7 is exposed to return lights of the irradiating lights within one exposure period within the one image pickup cycle. The CCD 7 photoelectrically converts light passing through the light-receiving side color filters 7*a* and obtains image signals of the individual colors in the one image pickup cycle. The image signals of the individual colors are combined, and an endoscopic image under special-light observation in the one image pickup cycle is obtained.

Note that although switching from extinction of LED1 to lighting of LED2 has been described as being performed at time t1 without a time lag in the present embodiment, the present invention is not limited to this. For example, a time lag may occur depending on performance of the CCD driver 13 in the processor 5. Note that a configuration intended to minimize occurrence of a time lag is desirable from a viewpoint of reducing color misregistration and image blurring in an endoscopic image.

Although a timing for lighting of LED2 is controlled with reference to the lighting period T1 for LED1 or timing t1 for extinction in the present embodiment, the present invention is not limited to this. For example, as shown in FIG. 1, an optical sensor 20 which detects light emitted from LED1 may detect extinction of LED1, and the timing for lighting of LED2 may be controlled on the basis of a result of the detection. That is, the timing for stopping of LED1 may be detected on the basis of a detection result from the optical sensor that detects light emitted from LED1 that is driven earlier, and the timing for lighting of LED2 may be controlled.

With the lighting control of LED1 and LED2 by the LED control section 17, the exposure period for the CCD 7 is equal to a sum of the lighting period T1 and the lighting period T2, as shown in FIGS. 2(*b*) and 2(*c*). An interval between exposure periods for the plurality of colors within the image pickup cycle S (see FIG. 2(*a*)) for the CCD 7 can be shortened.

For the reason, even if the distal end portion 2B incorporating the CCD 7 moves due to movement of a site to be observed, such as an organ at a site close to a heart quick in movement, while the site to be observed is observed, since the interval between the lighting periods for the plurality of LEDs within the image pickup cycle period S (see FIG. 2(*a*)) for the CCD 7 is short or there is little interval, image blurring occurring in an endoscopic image to be displayed on the monitor 4 can be reduced.

There is no time lag between extinction of LED1 and lighting of LED2 within the image pickup cycle S (see FIG. 2(*a*)) for the CCD 7, and even if a time lag occurs, the time lag can be kept within a short time period. Thus, even if the distal end portion 2B incorporating the CCD 7 moves due to movement of a site to be observed, such as an organ at a site close to a heart quick in movement, particularly while the site to be observed is observed, color misregistration occurring in an endoscopic image to be displayed on the monitor 4 can be reduced.

In the special-light observation mode, illuminating light of green (G) is obtained by causing white light from LED1 to transmit the optical filter 18 and converting the white light, and a loss in the amount of light occurs due to the conversion. To obtain illuminating light of bright green (G), LED1 thus needs to be driven with high output. In the present embodiment, the plurality of illumination sections are sequentially lighted within one image pickup cycle such that driving time periods for the plurality of LEDs do not overlap with each other. The configuration makes a load imposed on a power source for driving the LEDs lighter than a configuration which simultaneously drives the LEDs with high output and allows prevention of increase in power source size and increase in circuit complexity.

Thus, according to the first embodiment, the endoscope apparatus 1 that can obtain a bright high-quality endoscopic image with a simple configuration at low cost can be realized.

Figure 3:
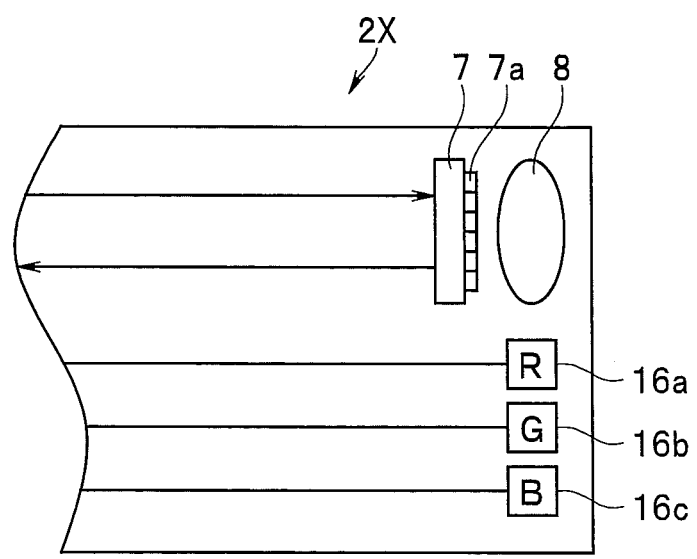
FIG. 3 is a configuration diagram showing a configuration of a first modification of an insertion portion distal end portion of the endoscope in FIG. 1.

Note that although a configuration in which the plurality of illumination sections are limited to the two LEDs, LED1 and LED2, and switching between the normal light observation mode and the special-light observation mode is performed is adopted in the present embodiment, for example, a configuration may be adopted in which three LEDs which emit lights of respective colors of R, G, and B are provided, and normal light observation can be performed by performing lighting control such that the LED control section 17 sequentially lights the LEDs of the respective colors of R, G, and B within one image pickup cycle, as in the special-light observation mode. As shown in a first modification in FIG. 3, three LEDs 16*a* to 16*c* which emit lights of respective colors of R, G, and B may be provided inside the distal end portion 2B of the endoscope 2, and the LED control section 17 may perform lighting control as described above. In the case as well, effects similar to the effects of the first embodiment are obtained.

Second Embodiment

Figure 4:
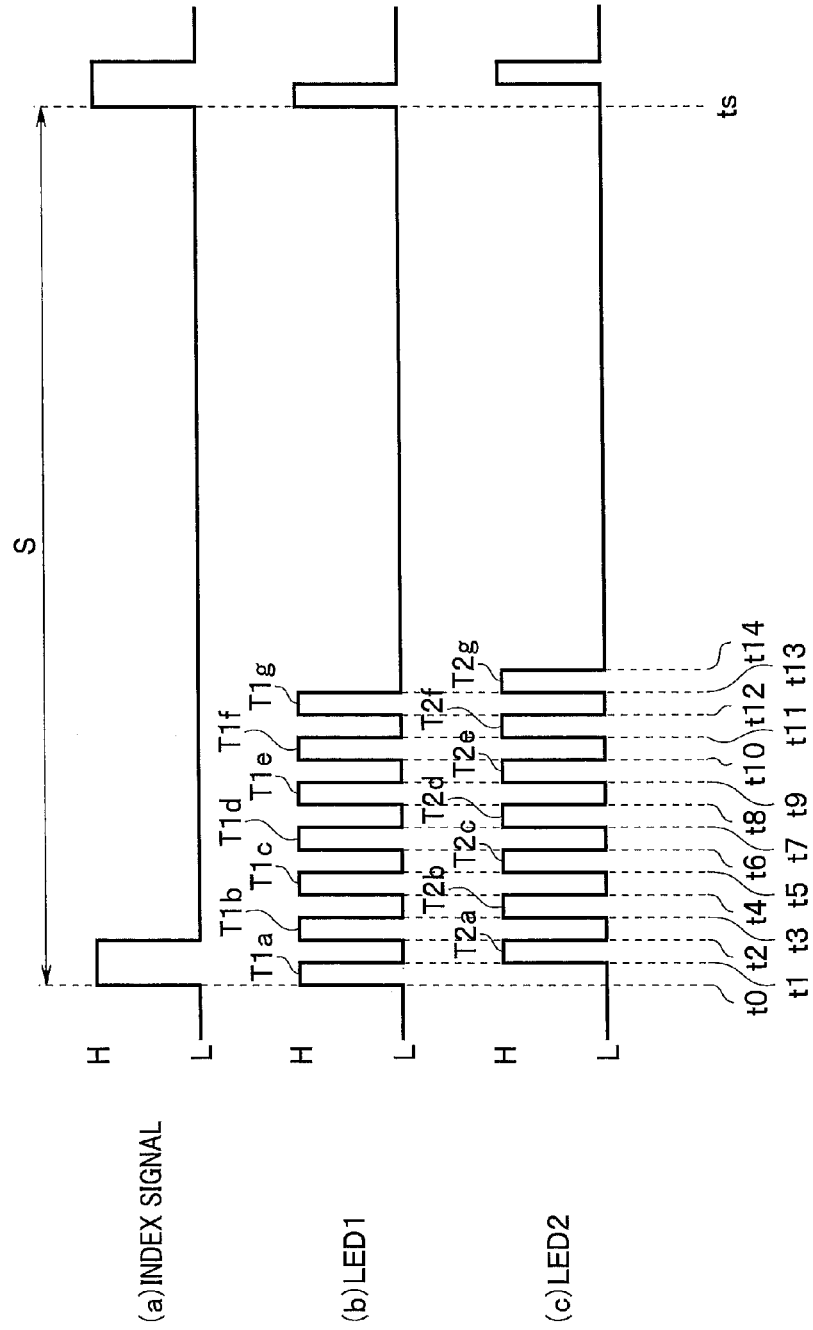
FIG. 4 are timing charts for explaining action of an endoscope apparatus according to a second embodiment of the present invention.
Figure 5:
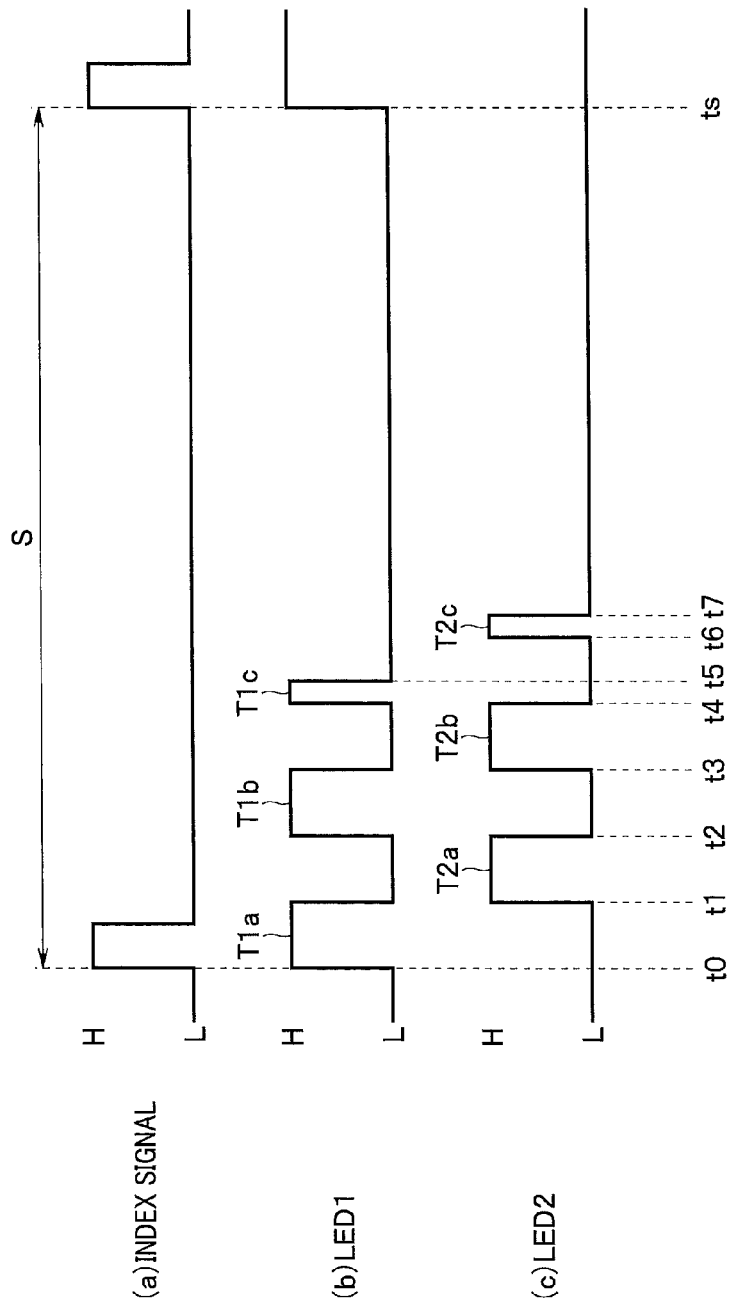
FIG. 5 is a timing chart showing a control example of an endoscope apparatus according to a second modification.

FIG. 4 are timing charts for explaining action of an endoscope apparatus according to a second embodiment of the present invention. FIG. 5 are timing charts showing a control example of an endoscope apparatus according to a second modification.

An endoscope apparatus 1 according to the present embodiment has a configuration similar to the configuration of the first embodiment. A method for controlling an LED control section 17 in a special-light observation mode in a light source apparatus 3, however, is different from the method in the first embodiment.

That is, in the endoscope apparatus 1 according to the present embodiment, the LED control section 17 performs control so as to drive at least two of a plurality of illumination sections a plurality of times within an image pickup cycle S.

More specifically, the LED control section 17 equally divides a lighting period T1 for LED1 and a lighting period T2 for LED2 which are calculated in advance on the basis of a brightness detection result and acquires divided lighting periods T1a to T1g and lighting periods T2a to T2g, as shown in FIG. 4.

That is, a sum of all the equally divided lighting periods T1a to T1g equals to the lighting period T1 (see FIG. 2) acquired in the first embodiment. A sum of all the equally divided lighting periods T2a to T2g equals to the lighting period T2 (see FIG. 2) acquired in the first embodiment.

As in the first embodiment, the LED control section 17 lights LED1 at time t0 when an index signal shown in FIG. 4(a) changes to "High" level (see FIG. 4(b)).

After a lapse of the lighting period T1a for LED1, i.e., at time t1, the LED control section 17 performs control so as to extinguish LED1 and at a same time light LED2, as shown in FIGS. 4(a) and 4(b).

After a lapse of the lighting period T2a for LED2, i.e., at time t2, the LED control section 17 performs control so as to extinguish LED2 and at a same time light LED1. After the time, the LED control section 17 similarly performs control so as to alternately light LED1 and LED2 in a manner corresponding to the individual lighting periods until lighting during the lighting period T1 g and lighting during the lighting period T2g are completed. That is, the LED control section 17 drives the plurality of LEDs a plurality of times such that each LED lights up alternately for a lighting time period obtained by equally dividing a corresponding one of respective driving time periods for the plurality of LEDs.

The configuration allows shortening of one lighting period for LED1 and LED2 and does not cause a time lag between a timing for extinction of LED1 and a timing for lighting of LED2.

Thus, in the endoscope apparatus 1 according to the second embodiment as well, occurrence of color misregistration and image blurring in an endoscopic image can be reduced, as in the first embodiment.

Note that although the endoscope apparatus 1 according to the present embodiment obtains the individual lighting periods by equally dividing the total lighting time period T1 for LED1 and the total lighting time period T2 for LED2 by a predetermined number within the image pickup cycle, the present invention is not limited to this. The total lighting time period T1 for LED1 and the total lighting time period T2 for LED2 may be divided by a given period, and lighting control of LED1 and LED2 may be performed in a manner corresponding to divided lighting periods, as shown in the second modification in FIG. 5. That is, the LED control section 17 drives the plurality of LEDs a plurality of times such that each of the two LEDs lights up alternately for a lighting time period which is obtained by dividing a corresponding one of respective driving time periods for the two LEDs by a predetermined period.

More specifically, as shown in FIG. 5, the LED control section 17 divides a lighting period T1 for LED1 and a lighting period T2 for LED2 which are calculated in advance on the basis of a brightness detection result by a given value and acquires divided lighting periods T1a, T1b, and T1c and lighting periods T2a, T2b, and T2c.

In the case, the lighting periods T1a and T1b have same durations, and a lighting period left over after the lighting periods T1a and T1b are subtracted from the lighting period T1 is the lighting period T1c. The lighting periods T2a and T2b have same durations, and a lighting period left over after the lighting periods T2a and T2b are subtracted from the lighting period T2 is the lighting period T2c.

That is, a sum of all the lighting periods T1a, T1b, and T1c divided by the given value equals to the lighting period T1 (see FIG. 2) acquired in the first embodiment. A sum of all the lighting periods T2a, T2b, and T2c divided by the given value equals to the lighting period T2 (see FIG. 2) acquired in the first embodiment.

As in the second embodiment, the LED control section 17 lights LED1 at time t0 when an index signal shown in FIG. 5(a) changes to "High" level (see FIG. 5(b)).

After a lapse of the lighting period T1a for LED1, i.e., at time t1, the LED control section 17 performs control so as to extinguish LED1 and at a same time light LED2, as shown in FIGS. 5(a) and 5(b).

After a lapse of the lighting period T2a for LED2, i.e., at time t2, the LED control section 17 performs control so as to extinguish LED2 and at a same time light LED1.

After a lapse of the lighting period T1b for LED1, i.e., at time t3, the LED control section 17 performs control so as to extinguish LED1 and at a same time light LED2.

After a lapse of the lighting period T2b for LED2, i.e., at time t4, the LED control section 17 performs control so as to extinguish LED2 and at a same time light LED1.

After a lapse of the lighting period T1c for LED1, i.e., at time t5, the LED control section 17 performs control so as to extinguish LED1. After the extinction, the LED control section 17 performs control so as to light LED2 and keep LED2 on during the left-over lighting period T2c shown between times t6 and t7.

Thus, according to the second modification, an interval between adjacent ones of lighting periods for the plurality of LEDs can be shortened without equally dividing each lighting period by a predetermined number, and no time lag occurs between lighting of LED1 and lighting of LED2. Occurrence of color misregistration and blurring in an endoscopic image can thus be reduced, as in the second embodiment.

Note that although control of the light source unit 16 in the endoscope apparatus 1 has been described as being performed by the LED control section 17 in the first and second embodiments, the endoscope apparatus 1 may be configured such that the control is performed by the control section 15 in the processor 5. Alternatively, the control section 15 in the processor 5 and the LED control section 17 in the light source apparatus 3 may be configured as one control section to control the light source unit 16.

The endoscope apparatus 1 according to the present invention is configured such that the two LEDs, LED1 and LED2, are provided to perform both of normal light observation and special-light observation, such as narrow band observation. Even if either one of the LEDs fails during observation, illuminating light required to, e.g., remove the insertion portion 2A from inside a body cavity can be secured. Such configurations are disclosed in FIGS. 6 to 9.

First Disclosed Example

Figure 6:
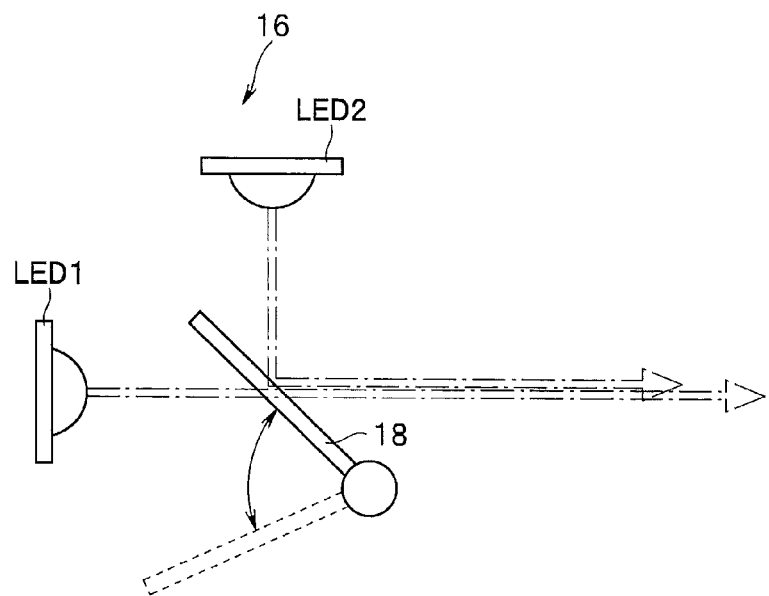
FIG. 6 is a schematic diagram showing a configuration of a light source unit according to a first disclosed example.
Figure 7:
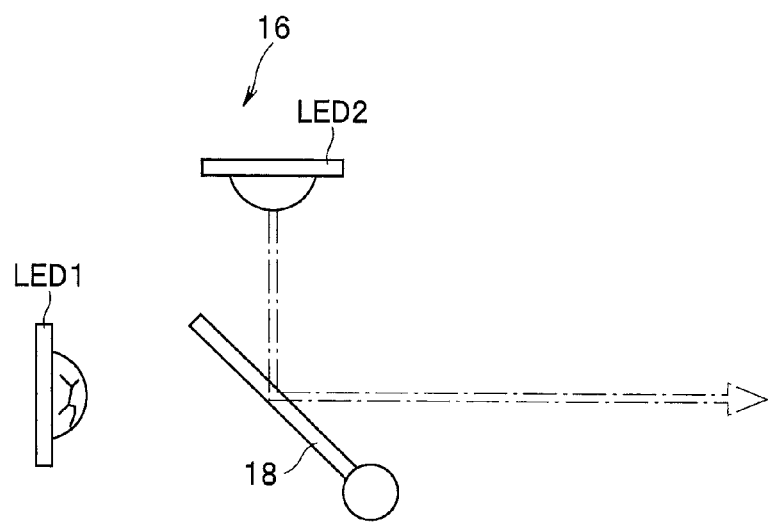
FIG. 7 is a schematic diagram showing an operating condition when LED1 in FIG. 6 is in failure.

FIG. 6 is a schematic diagram showing a configuration of a light source unit according to a first disclosed example. FIG. 7 is a schematic diagram showing an operating condition when LED1 in FIG. 6 is in failure.

The light source unit 16 in the light source apparatus 3 shown in FIG. 6 is substantially similar to the light source unit 16 in the first embodiment. That is, when the light source unit 16 performs special-light observation, such as narrow band observation, the optical filter 18 that is arranged in a manner as shown in FIG. 6 converts white light from LED1 into green (G) and irradiates the lens 19 with the green light, and reflects violet light from LED2 and irradiates the lens 19 with the violet light. With the configuration, green (G) light and violet light required for special-light observation are obtained.

When the light source unit 16 performs normal light observation, since the optical filter 18 retreats from inside an optical path for LED1 and is arranged at a retreat position (a position indicated by a broken line in FIG. 6), the light source unit 16 irradiates the lens 19 with white light only from LED1. With the configuration, white light required for normal light observation is obtained.

Even if illuminating light as white light or green (G) light is not obtained due to, e.g., a failure of LED1 during observation, since the optical filter 18 is arranged at a position as shown in FIG. 7, the endoscope apparatus 1 according to the present example can perform irradiation only with violet light from the distal end portion 2B that is used at least in narrow band observation.

Since an object can be irradiated only with violet light from the distal end portion 2B, illuminating light required to, e.g., remove the insertion portion 2A from inside a body cavity can be secured.

Second Disclosed Example

Figure 8:
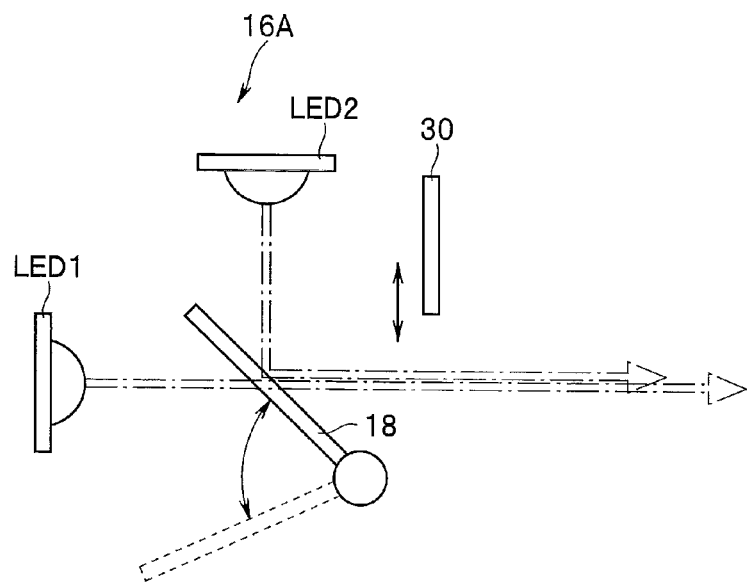
FIG. 8 is a schematic diagram showing a configuration of a light source unit according to a second disclosed example.
Figure 9:
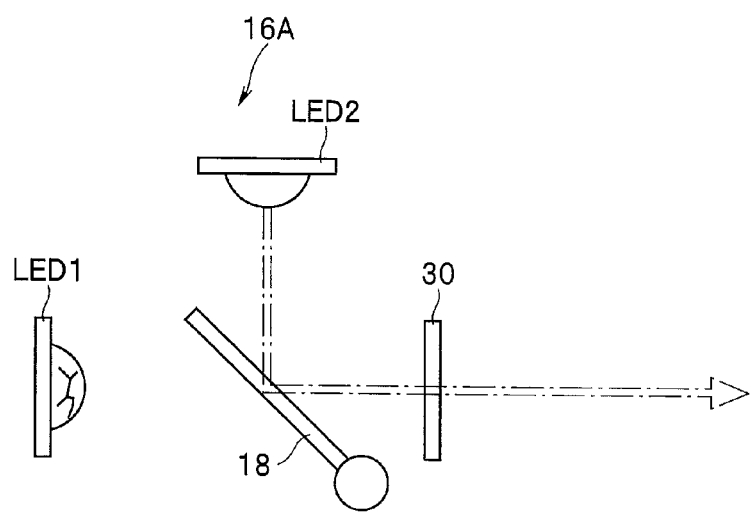
FIG. 9 is a schematic diagram showing an operating condition when LED1 in FIG. 8 is in failure.

FIG. 8 is a schematic diagram showing a configuration of a light source unit according to a second disclosed example. FIG. 9 is a schematic diagram showing an operating condition when LED1 in FIG. 8 is in failure.

A light source unit 16A of the light source apparatus 3 shown in FIG. 8 is substantially similar to the light source unit 16 in the first disclosed example but is different in that the light source unit 16A is configured to obtain not violet light but white light even if LED1 fails.

More specifically, as shown in FIG. 8, the light source unit 16A is provided with a fluorescence filter 30 which can move to be arranged in an optical path for violet light from LED2 that is reflected from the optical filter 18.

As shown in FIG. 9, in the event of a failure of LED1, the fluorescence filter 30 is arranged in the optical path for violet light from LED2 that is reflected from the optical filter 18 and has an optical property of converting taken-in violet light into white light and emitting the white light.

That is, when normal light observation or special-light observation is performed, the fluorescence filter 30 retreats from inside the optical path for LED2 and is arranged at a retreat position, as shown in FIG. 8.

For example, if LED1 fails during manipulation, and illuminating light as white light or green (G) light is not obtained, the fluorescence filter 30 is arranged by drive means (not shown) in the optical path for violet light from LED2 that is reflected from the optical filter 18, as shown in FIG. 9.

For the reason, the fluorescence filter 30 can convert taken-in violet light into white light and irradiate the lens 19 with the white light. Since irradiation not with violet light in the first disclosed example but with white light from the distal end portion 2B can be performed, white light that is normal light can be secured, as in normal light observation. Thus, manipulation can be continuously performed without interruption.

As has been described above, according to the endoscope apparatuses according to the above-described embodiments, a bright high-quality endoscopic image can be obtained with a simple configuration at low cost.

The present invention is not limited to the above-described embodiments and modifications, and various changes, alterations, and the like can be made without departing from the scope of the present invention.

What is claimed is:
1. An endoscope apparatus comprising:
a timing generator which outputs an index signal in predetermined cycles;
an image pickup section including a solid image pickup device in which color filters of a plurality of colors are provided at front faces of a plurality of light-receiving devices, the image pickup section being so as to pick up an image of a site to be observed for each of image pickup cycles, the each of the image pickup cycles being a period from when the index signal is inputted to when a next index signal is inputted;
a first light-emitting device which emits first illuminating light with which the site to be observed is irradiated;
a second light-emitting device which emits second illuminating light with which the site to be observed is irradiated, the second illuminating light having a color different from a color of the first illuminating light;
an illumination control section which drives the first light-emitting device such that the site to be observed is irradiated with the first illuminating light, and drives the second light-emitting device such that irradiation of the site to be observed with the second illuminating light is started with reference to a timing at which the irradiation with the first illuminating light is finished, within one of the image pickup cycles; and
an image pickup control section which controls the image pickup section so as to collectively read out, within one exposure period in one of the image pickup cycles, image signals of respective colors obtained by the light-receiving devices performing photoelectric conversion on return lights which are returned from the site to be observed irradiated with the first and second illuminating lights and which have passed through the color filters of the plurality of colors,
wherein the illumination control section drives the first and second light-emitting devices, within one of the image pickup cycles, such that the timing at which the irradiation with the first illuminating light by the first light-emitting device is finished is substantially at a same time as a timing at which the irradiation with the second illuminating light by the second light-emitting device is started, and the timing for stopping of the first light-emitting device is detected on the basis of a detection result from an optical sensor which detects light emitted from the first light-emitting device.

2. The endoscope apparatus according to claim 1, wherein the illumination control section drives the first and second light-emitting devices a plurality of times within the image pickup cycle.

3. The endoscope apparatus according to claim 2, wherein the illumination control section drives the first and second light-emitting devices the plurality of times such that each of the first and second light-emitting devices lights up alternately for a corresponding one of lighting time periods obtained by equally dividing the irradiation time periods by the first and second light-emitting devices.

4. The endoscope apparatus according to claim 2, wherein the illumination control section drives the first and second light-emitting devices the plurality of times such that each of the first and second light-emitting devices lights up alternately for a corresponding one of lighting time periods obtained by dividing the irradiation time periods by the first and second light-emitting devices by a predetermined period.

5. The endoscope apparatus according to claim 1, wherein the illumination control section variably controls irradiation time periods by the first and second light-emitting devices within one of the image pickup cycles in order to adjust an amount of exposure for each one of the image pickup cycles.

6. The endoscope apparatus according to claim 5, wherein the illumination control section variably controls the irradiation time periods by the first and second light-emitting devices on the basis of brightness of an observed image for one field or one frame which is obtained by the image pickup section.

7. The endoscope apparatus according to claim 6, wherein the illumination control section calculates the irradiation time periods by the first and second light-emitting devices on the basis of a difference between brightness of a field or a frame obtained in one of the image pickup cycles and brightness of a field or a frame in an image pickup cycle previous to the one of the image pickup cycles.

8. The endoscope apparatus according to claim 1, wherein
the endoscope apparatus has a plurality of observation modes, and
whether to light each of the first and second light-emitting devices is controlled according to the observation modes.

9. The endoscope apparatus according to claim 1, wherein the index signal is a vertical synchronizing signal, which is produced in cycles of once an image of the site to be observed for one frame or one field as the predetermined cycles.

10. The endoscope apparatus according to claim 1, further comprising an optical filter disposed on a side where the first illuminating light is emitted, wherein, in the second observation mode, a portion of the first illuminating light is passed through the optical filter and the site to be observed is irradiated with the first illuminating light, and, in the first observation mode, the first illuminating light is not passed through the optical filter and the site to be observed is directly irradiated with the first illuminating light.

11. The endoscope apparatus according to claim 10, wherein
the first illuminating light is white light,
the second illuminating light is a first narrow band light having a first wavelength, and
in the second observation mode, the optical filter receives the white light and emits a second narrow band light having a second wavelength different from the first wavelength.

* * * * *